US009409928B2

United States Patent
Tang et al.

(12) United States Patent
(10) Patent No.: US 9,409,928 B2
(45) Date of Patent: *Aug. 9, 2016

(54) AGGREGATION INDUCED EMISSION ACTIVE CYTOPHILIC FLUORESCENT BIOPROBES FOR LONG-TERM CELL TRACKING

(71) Applicant: The Hong Kong University of Science and Technology, Hong Kong (CN)

(72) Inventors: Benzhong Tang, Hong Kong (CN); Ka Ming Ng, Hong Kong (CN); Qian Luo, Singapore (SG); Yong Yu, Hong Kong (CN); Yuning Hong, Hong Kong (CN); Jianzhao Liu, Hong Kong (CN); Sijie Chen, Hong Kong (CN); Wing Yip Lam, Hong Kong (CN)

(73) Assignee: THE HONG KONG UNIVERSITY OF SCIENCE AND TECHNOLOGY, Kowloon (HK)

( * ) Notice: Subject to any disclaimer, the term of this patent is extended or adjusted under 35 U.S.C. 154(b) by 231 days.

This patent is subject to a terminal disclaimer.

(21) Appl. No.: 13/649,819

(22) Filed: Oct. 11, 2012

(65) Prior Publication Data

US 2013/0089889 A1 Apr. 11, 2013

Related U.S. Application Data

(60) Provisional application No. 61/627,336, filed on Oct. 11, 2011.

(51) Int. Cl.

| | |
|---|---|
| ***C12Q 1/04*** | (2006.01) |
| ***C07F 7/08*** | (2006.01) |
| ***B82Y 15/00*** | (2011.01) |
| *G01N 21/64* | (2006.01) |

(52) U.S. Cl.

CPC ............... *C07F 7/0818* (2013.01); *B82Y 15/00* (2013.01); *G01N 21/6458* (2013.01); *G01N 2021/6439* (2013.01); *Y10T 428/2982* (2015.01)

(58) Field of Classification Search

CPC ..... B82Y 15/00; C07F 7/0818; C07F 7/0827; G01N 2021/6439; G01N 21/6458

See application file for complete search history.

(56) References Cited

U.S. PATENT DOCUMENTS 5,362,628 A 11/1994 Haugland et al.

OTHER PUBLICATIONS

Yu et al. Sci. China Series B: Chemistry (Jan. 2009) 52(1): 15-19.*
Chen et al. Chem. Mater. (2003) 15: 1535-1436.*
He et al. J. Mater. Chem. (2009) 19: 7347-7353.*
Yu et al. Advanced Materials (Aug. 2011; published online Jun. 14, 2011) 23: 3298-3302.*
Farrell, et al., "Effects of iron oxide incorporation for long term cell tracking on MSC differentiation in vitro and in vivo," Biochemical and Biophysical Research Communications, (2008), vol. 369, pp. 1076-1081.

* cited by examiner

*Primary Examiner* — Susan Hanley

(74) *Attorney, Agent, or Firm* — Nath, Goldberg & Meyer; Joshua B. Goldberg; Christopher Thomas

(57) ABSTRACT

Fluorescent bioprobes comprising luminogen formed nanoparticles comprising luminogens with aggregation-induced emission (AIE) properties, which can be used for long-term cell tracking. The luminogens are nonemissive in organic solution but become highly emissive when aggregated in aqueous solution. The fluorescent molecules can readily pass through cell membranes, stain only the cell cytoplasm, and form highly emissive nanoaggregates in aqueous media without any obvious cytoxicity in the living cells. Furthermore, the molecules can be retained inside the cells without noticeable leakage to the outside. Therefore, these AIE-based compounds can be used as selective and cell-compatible fluroescent bioprobes for long-term live cell tracking and imaging.

14 Claims, 7 Drawing Sheets

AGGREGATION INDUCED EMISSION ACTIVE CYTOPHILIC FLUORESCENT BIOPROBES FOR LONG-TERM CELL TRACKING

RELATED APPLICATIONS

The present patent application claims priority to Provisional Patent Application No. 61/627,336 filed Oct. 11, 2011, which was filed by the inventors hereof and is incorporated by reference herein in its entirety.

TECHNICAL FIELD

The present subject matter relates to fluorescent bioprobes comprising luminogens that exhibit aggregation induced emission (AIE). The luminogens can be formulated as uniformly sized nanoparticles with high brightness and low cytotoxicity. These AIE-active luminogen formed nanoparticles can be utilized as probes for long term cellular tracking.

BACKGROUND

Fluorescent bioprobes have made important contributions to advancing our knowledge in life science, thanks to their unrivalled ability to image and monitor biological structures and processes in living systems. Typical materials used as biosensors include natural polymers, inorganic nanoparticles, and organic dyes. Green fluorescent protein (GFP), for example, has been used as a reporter of expression for morphological differentiation. The biosensing process, however, requires complicated and time-consuming transfection procedures, which can lead to unexpected morphologies and undesired abnormality in the target cells. Inorganic nanoparticles, such as quantum dots (QDs), are highly luminescent and resistant to photobleaching but limited in variety and inherently toxic to living cells, because QDs are commonly made of heavy metals and chalcogens (e.g., CdSe and PbS).

Organic dyes are rich in variety and have been widely used as readily processable light-emitting materials, particularly in the area of organic optoelectronics. Due to their poor miscibility with water, organic dyes are prone to aggregate in aqueous media, which normally weakens their light emissions. This effect is commonly known as aggregation-caused quenching (ACQ). Incorporation of cationic (e.g., aminium) or anionic (e.g., sulfonate) groups into organic dyes can improve their miscibility with physiological buffer. The charged species repel each other and prevent the dye molecules from aggregating, hence alleviating the ACQ effect.

Although the ionic groups can help enhance their solubility in water, the dyes are still inclined to aggregate at high concentrations due to the hydrophobicity of their aromatic cores. This is likely why dyes are commonly used in only trace amounts (often at the nM level). At high concentrations, the electric charges of the ionized dyes may affect membrane potentials, perturb intracellular physiology and even cause cell lyses. On the other hand, at low dye concentrations, the fluorescence signals are weak and the small amount of dye molecules that enter cells are easily photobleached during the imaging process. Furthermore, during cell division and when confluent cells are passed, the intracellular dye molecules may diffuse back to the extracellular media due to the concentration gradient. This results in a decrease in the fluorescence of the stained cells and a concurrent increase in the solution fluorescence (or background emission) as well as random staining in co-culture systems of different types of cell lines.

One way to keep the dye molecules inside cells and to prevent them from leaking to media is to fix them through bioconjugation. This necessitates further attachment of new reactive groups to the ionic dyes. Since the bioconjugations are usually conducted in situ under physiological conditions, the reactions are normally incomplete, wherein the extent of chemical transformation is unknown. This makes it difficult to learn how and to what extent the reactions affect the metabolism and physiology of the living cells stained by the conjugation processes. The unconjugated dyes can escape from the cells, and even the conjugated dyes can be released back to the culture media, because the biomolecular units responsible for the bioconjugation may be degraded by the enzymatic reactions in the incubation processes and by the phototoxic effects of the bioimaging process.

Accordingly, there is a great need for the development of fluorescent bioprobes with high biological compatibility, strong photobleaching resistance, efficient light emission, and that are nontoxic to live cells, and have the ability to stay inside live cells for a long period of time without leaking out into the culture media.

SUMMARY

The present subject matter relates to fluorescent bioprobes comprising luminogen formed nanoparticles that exhibit aggregation-induced emission (AIE) properties. In contrast to the conventional GFP- and QD-based biosensors, the fluorescent bioprobes described herein are easy to use and nontoxic to living cells. The instant bioprobes are also superior to conventional organic dye systems: they are ACQ-free, electrically neutral, cytocompatible, and usable at high concentrations. Furthermore, the luminogen based bioprobes can stay inside live cells for a long period of time without leaking out into culture media, thus enabling long-term cell tracing over multiple passages as well as process monitoring of a whole biological event. Due to the fluorescent bioprobes' ability to stay inside live cells for long periods of time, they do not contaminate cells of different types in a co-culture system. This permits growth tracking of a specific cell line.

Different from the CellTracker and MitoTracker bioprobes, the fluorescence turn-on and cellular internalization are realized herein through physical processes and the aggregates are stable under ambient conditions and need do not need to be shielded from air and moisture and stored at low temperatures. The nanoaggregates are indelibly retained inside the living cells, owing to their cytophilic nature and hydrophobic interactions with lipids, lipoproteins, etc. The fluorescent stains are carried to daughter cells and remain visible through four generations. These features make the fluorescent bioprobes comprising AIE luminogens applicable for an array of biosensing applications.

In one embodiment, the present subject matter relates to a fluorescent bioprobe comprising luminogen formed nanoparticles for cellular imaging and long term cellular tracking comprising one or more luminogens that exhibit aggregation-induced emission properties; wherein the luminogen formed nanoparticles are fully retained inside living cells and have a fluorescence emission; and wherein the luminogens have a backbone structure selected from the group consisting of:

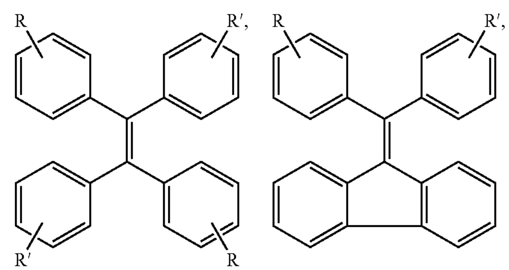

-continued

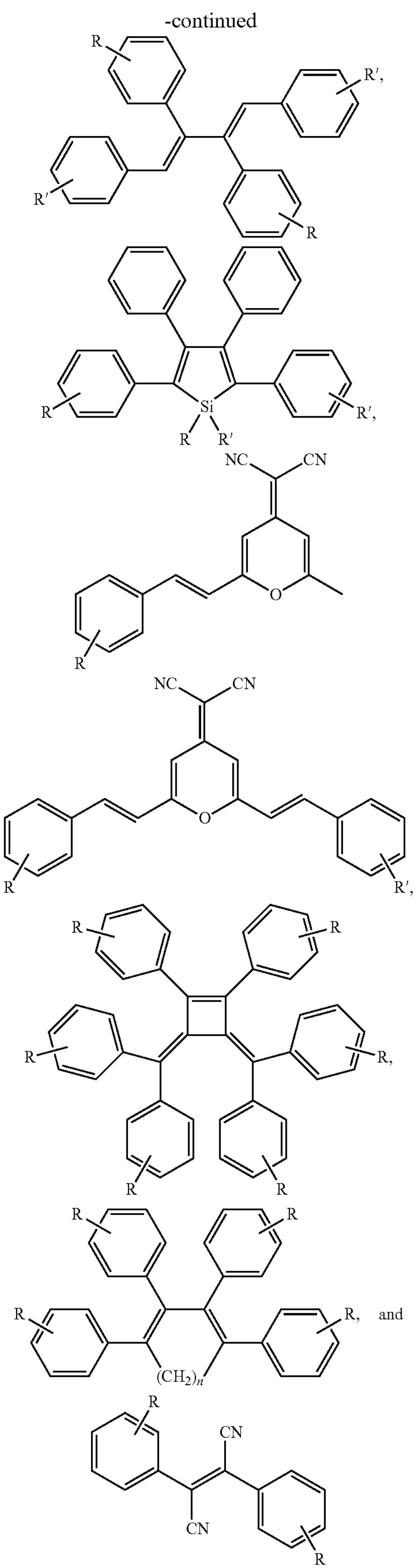

wherein R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20, wherein when both the R and R' groups attached to the Si atom are $C_6H_5$, at least one of the R and R' groups attached to the phenyl rings is other than H.

Another embodiment of the present subject matter relates to a method of preparing the fluorescent bioprobes comprising: (a) preparing an organic solution of the luminogens; and (b) mixing the organic solution into an aqueous medium.

Another embodiment relates to a method of in vitro cellular imaging comprising contacting target cells with the fluorescent bioprobes and detecting cellular fluorescence.

BRIEF DESCRIPTION OF THE DRAWINGS

Various embodiments will be described in detail with reference to the accompanying drawings.

DETAILED DESCRIPTION

Definitions

Figure 1:
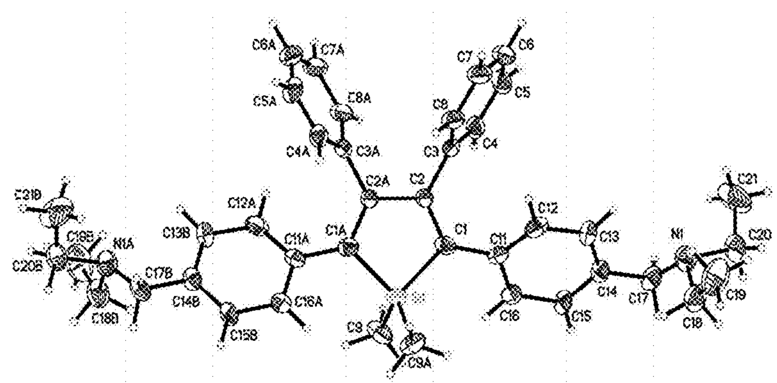
FIG. 1 illustrates the Oak Ridge Thermal Ellipsoid Plot (ORTEP) of Silole-$C_1$.
Figure 2:
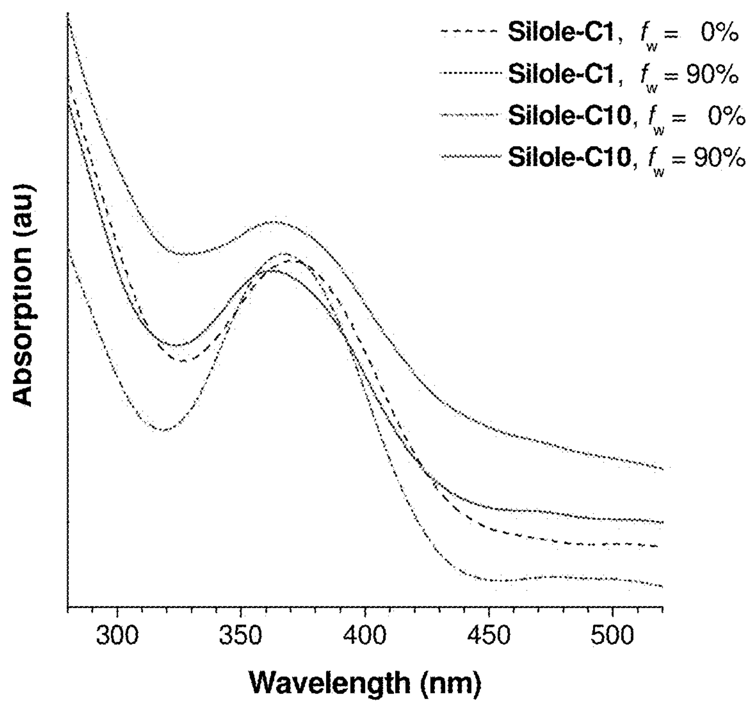
FIG. 2 illustrates the absorption spectrum of Silole-$C_1$ and Silole-$C_{10}$ in THF/water mixtures with different water fractions ($f_w$). [Silole-$C_1$]=10 μM, [Silole-$C_{10}$]=10 μM.

All technical and scientific terms used herein have the same meanings as commonly understood by someone ordinarily skilled in the art to which the present subject matter belongs. The following definitions are provided for clarity.

The phrase "π-conjugated luminogen" as used herein refers to any luminogen covalently bonded with alternating single and double bonds in an organic compound.

The term "$\lambda_{ex}$" as used herein refers to excitation wavelength.

The phrase "aggregation caused quenching" or "ACQ" as used herein refers to the phenomenon wherein the aggregation of π-conjugated luminogens significantly decreases the fluorescence intensity of the luminogens. The aggregate formation is said to "quench" light emission of the luminogens.

The phrase "aggregation induced emission" or "AIE" as used herein refers to the phenomenon manifested by compounds exhibiting enhancement of light-emission upon aggregation in the amorphous or crystalline (solid) states whereas they exhibit weak or almost no emission in dilute solutions.

The term "biomacromolecule" as used herein refers to a very large molecule, such as a protein, nucleic acid, or polysaccharide of biological origin.

The term "DMF" as used herein refers to dimethylformamide, which is an organic compound with the formula $(CH_3)_2NC(O)H$. It is a common solvent for chemical reactions.

The term "DMSO" as used herein refers to dimethyl sulfoxide, which is an organic compound having the formula $(CH_3)_2SO$. It is a common solvent for chemical reactions.

The term "EDTA" as used herein refers to ethylenediaminetetraacetic acid. It is a polyamino carboxylic acid and a colorless, water-soluble solid.

The phrase "emission intensity" as used herein refers to the magnitude of fluorescence/phosphorescence normally obtained from a fluorescence spectrometer or a fluorescence microscopy measurement.

The term "luminogen" as used herein refers to a chemical compound that manifests luminescence.

The term "nanoparticle" as used herein refers to any microscopic particle or particle population having a mean diameter of about 100 or less nanometers (nm); less than about 90 nm; less than about 80 nm; less than about 70 nm; less than about 60 nm; less than about 50 nm in diameter; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

The phrase "quantum dots" as used herein refers to a type of matter, i.e., a semiconductor, whose excitons are confined in all three spatial dimensions. Quantum dots can be semiconductors whose electronic characteristics are closely related to the size and shape of the individual crystal. Generally, the smaller the size of the crystal, the larger the band gap, i.e., the difference in energy between the highest valence band and the lowest conduction band becomes greater. Therefore more energy is needed to excite the dot, and concurrently, more energy is released when the crystal returns to its resting state.

The term "a" or "an" as used herein includes the singular and the plural, unless specifically stated otherwise. Therefore, the term "a," "an," or "at least one" can be used interchangeably in this application.

Throughout the application, descriptions of various embodiments use the term "comprising;" however, it will be understood by one of skill in the art, that in some specific instances, an embodiment can alternatively be described using the language "consisting essentially of" or "consisting of."

For the purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a fluorescent bioprobe comprising luminogen formed nanoparticles for cellular imaging and long term cellular tracking comprising one or more luminogens that exhibit aggregation-induced emission properties; wherein the luminogen formed nanoparticles are fully retained inside living cells and have a fluorescence emission; and wherein the luminogens have a backbone structure selected from the group consisting of:

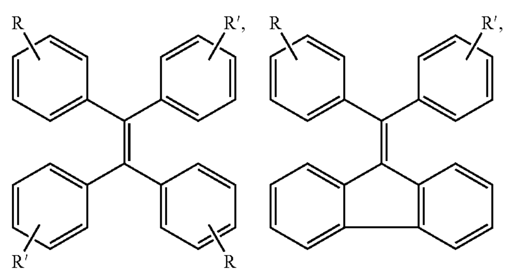

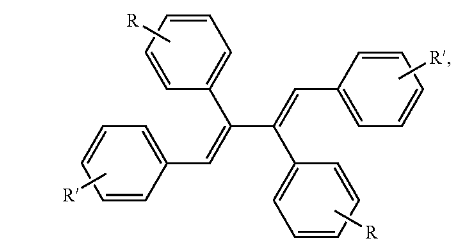

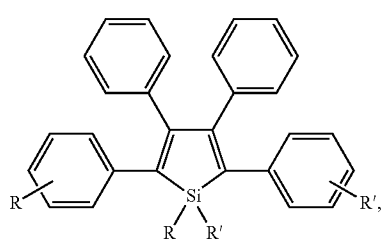

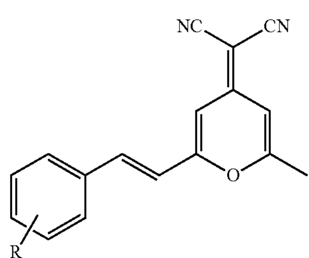

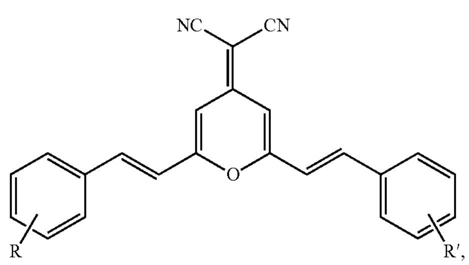

-continued

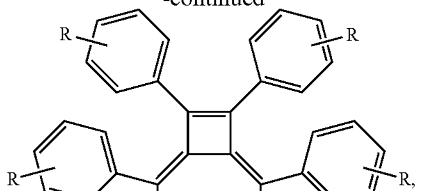

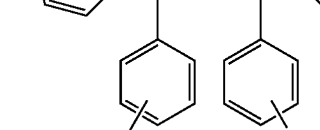

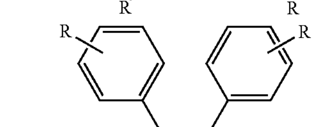

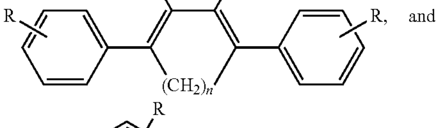

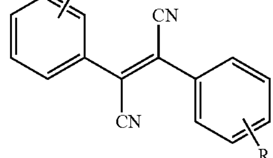

wherein R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_m$, $C_6H_5$, and $O(CH2)_n$; and n, m independently=an integer from 0 to 20, wherein when both the R and R' groups attached to the Si atom are $C_6H_5$, at least one of the R and R' groups attached to the phenyl rings is other than H.

In one embodiment, the AIE luminogens are selected from the group consisting of Silole-$C_1$ and Silole-$C_{10}$, the chemical structures of which are shown below.

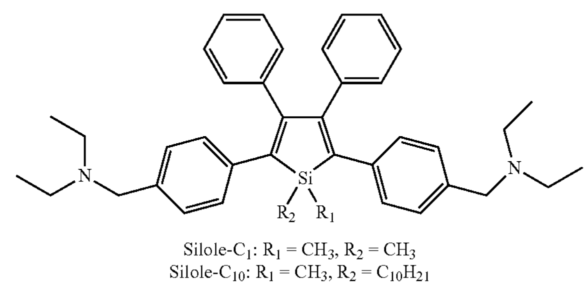

Silole-$C_1$: $R_1 = CH_3$, $R_2 = CH_3$
Silole-$C_{10}$: $R_1 = CH_3$, $R_2 = C_{10}H_{21}$ Silole-$C_1$ and Silole-$C_{10}$ were synthesized via the chemical reaction scheme, shown below.

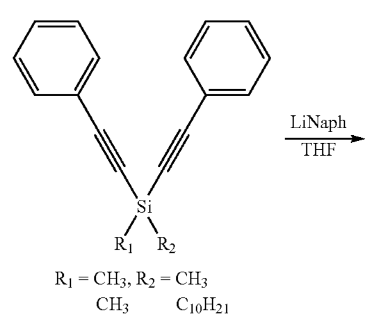

-continued

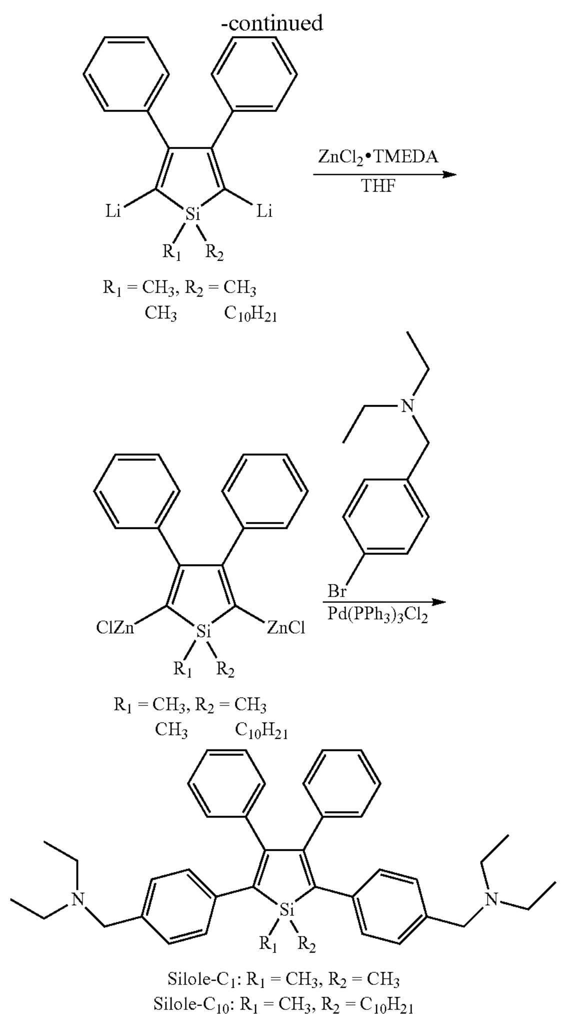

The luminogens are nonemissive in organic solution but become highly emissive when aggregated in aqueous solution. The fluorescent molecules can readily pass through cell membranes, stain only the cell cytoplasm, and form highly emissive nanoaggregates in aqueous media without any obvious cytoxicity to the living cells. Furthermore, the molecules can be retained inside the cells without noticeable leakage to the outside. Therefore, these AIE-based compounds can be used as selective and cell-compatible fluroescent dyes for long-term live cell tracking and imaging.

In one embodiment, the luminogen formed nanoparticles are 1 nm to 100,000 nm in size. In another aspect of the present subject matter, the luminogens comprise any aggregation-induced emission molecule that has noncovalent interactions, including hydrophobic interactions, with biomolecules inside cells.

In another embodiment, the fluorescence emission of the luminogen formed nanoparticles is further amplified by applying one or more of (a) a conjugated polymer as a fluorescence resonance energy transfer donor or (b) an arginine-glycine-aspartic acid peptide as a bio-recognition reagent functionalized on a surface of the nanoparticle.

Another embodiment of the present subject matter relates to a method of preparing the fluorescent bioprobes comprising: (a) preparing an organic solution of the luminogens; (b) mixing the organic solution into an aqueous medium; and (c) removing the organic solvent to form the luminogen formed nanoparticles. In one aspect the organic solution can comprise DMSO or DMF.

In another embodiment, a method of preparing the fluorescent bioprobes further comprises fabricating the luminogen formed nanoparticles with any molecule that can specifically target cancer cells or amplify the fluorescence imaging.

In one aspect, the present luminogen formed nanoparticles show excellent permeability, biocompatibility and AIE in vitro. The hydrophobic molecules with AIE properties can be used at extremely high concentrations without any self-quenching effect. The nanoaggregates formed by AIE luminogens in the growth medium are internalized by the cells and settle in the organelles via physical processes but not chemical reactions. These benign interactions with the cells endow AIE luminogens with superb cytocompatibility. The cytophilic nature of the AIE dyes and their hydrophobic interactions with the membrane-enclosed organelles make them leak-free inside the cells and enable the tracking of live cells for a period close to 100 hours.

Another embodiment relates to a method of in vitro cellular imaging comprising contacting target cells with the fluorescent bioprobes and detecting cellular fluorescence. In one aspect, the present luminogen formed nanoparticles show staining effects from cytoplasmic areas of cells. In an additional aspect, the luminogen formed nanoparticles can be used in large quantities and can stay inside live cells for long periods of time without leaking out into culture media.

In a further embodiment, the target cells are live cells. In this embodiment, the fluorescent bioprobes are capable of staying inside the target cells for at least 95 hours without leaking out into the culture medium. In another aspect, the fluorescent bioprobes are capable of staying inside the target cells for at least 4 passages without leaking out into the culture medium. In another embodiment, the target cells are cancer cells or cells that can preferentially accumulate in tumors. In another embodiment, the target cells are selected from the group consisting of HeLa cells and HEKT-293 cells. In one aspect, the method of in vitro cellular imaging further comprises determining whether a tumor or cancer cells are present. In another aspect, the in vitro cellular imaging further comprises live cell tracking. Finally, in yet another aspect, the in vitro cellular imaging comprises long term cellular tracking.

EXAMPLES

The examples below demonstrate various embodiments of the present subject matter.

THF (Labscan) was distilled under nitrogen from sodium benzo-phenone ketyl immediately prior to use. MitoTracker Red CMXRos (MTR), MitoTracker Green FM (MTG), and other bioimaging reagents were purchased from Invitrogen. Other chemicals, reagents and solvents used in this study were all purchased from Aldrich. $^{1}H$ and $^{13}C$ NMR spectra were measured on a Bruker ARX 400 NMR spectrometer using $CDCl_3$ as solvent. High-resolution mass spectra (HRMS) were taken on a Finnigan TSQ 7000 triple quadrupole spectrometer in a MALDI-TOF mode. UV spectra were measured on a Milton Roy Spectronic 3000 Array spectrophotometer. Fluorescence (FL) spectra were recorded on a Perkin-Elmer LS 55 spectrofluorometer. FL quantum yields OF) of amorphous powders of siloles were measured using C-701 Time-Resolved Spectrofluorometer with the integrating sphere as accessory following a literature procedure.

Morphologies of nanoaggregates in aqueous media were measured on JOEL 2010 TEM and JOEL 6700F SEM. Samples were prepared by dropping copper 400-mesh carrier grids covered with carbon-coated formvar films into the silole nanoaggregates dispersed in THF/water and DMSO/water mixtures and removing the solvent from the frozen specimen by a freeze-drier. Particle sizes and zeta potentials of the nanoaggregates were determined in THF/water or DMSO/ phosphate buffered saline (PBS; pH=7.4) mixture with a water content of 99.9% at room temperature using a Zeta-Plus Potential Analyzer. Single crystal X-ray diffraction (XRD) intensity data were collected at 100 K on a Bruker-Nonices Smart Apex CCD diffractometer with graphite monochromated Mo Kα radiation. Processing of the intensity data was carried out using the SAINT and SADABS routines, and the structure and refinement were conducted by the SHELTL suite of X-ray programs (version 6.10).

Example 1

Synthesis of Silole-$C_1$ and Silole-$C_{10}$

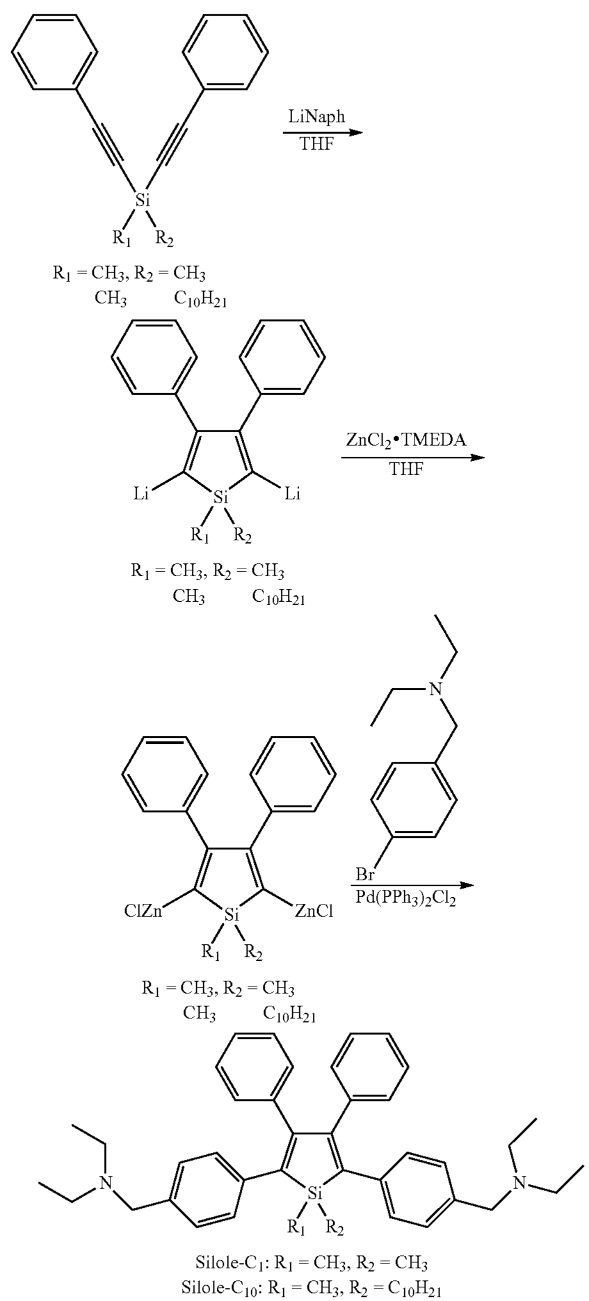

Silole derivative Silole-$C_1$ was synthesized according to the chemical reaction, as shown in the reaction scheme above. 0.056 g (8 mmol) of lithium wire and 1.04 g (8 mmol) of naphthalene in 8 mL of dry THF were added into a 50 mL round bottom flask. After stirring at room temperature under nitrogen for 3 h, a deep green solution of lithium naphthalene was formed, which was added dropwise to a solution of 0.52 g (2 mmol) of bis(phenylethynyl)-dimethylsilane in 5 mL of THF over 2 min at room temperature. The mixture was stirred for 1 h, cooled to 0° C., and diluted with 10 mL of THF. After addition of 2 g (8 mmol) of $ZnCl_2$.TMEDA, the black suspension was stirred for an additional hour at room temperature. A solution of 2-(4-bromophenyl)ethyldiethylamine (1.57 g, 6.6 mmol) and 0.08 g (0.1 mmol) of $PdCl_2(PPh_3)_2$ in 10 mL of THF was then added. After being refluxed overnight and cooled to room temperature, 10 mL of 3 M HCl solution was added and the resultant mixture was extracted with dichloromethane (DCM). The combined organic layer was washed with brine and dried over $MgSO_4$. After solvent evaporation under reduced pressure, the crude product was purified by a silica gel column using ethyl acetate/hexane (1:9 v/v) as eluent. A yellow powder of Silole-$C_1$ was obtained in 50% yield. Likewise, Silole-$C_{10}$ was prepared in 40% yield.

Figure 3:
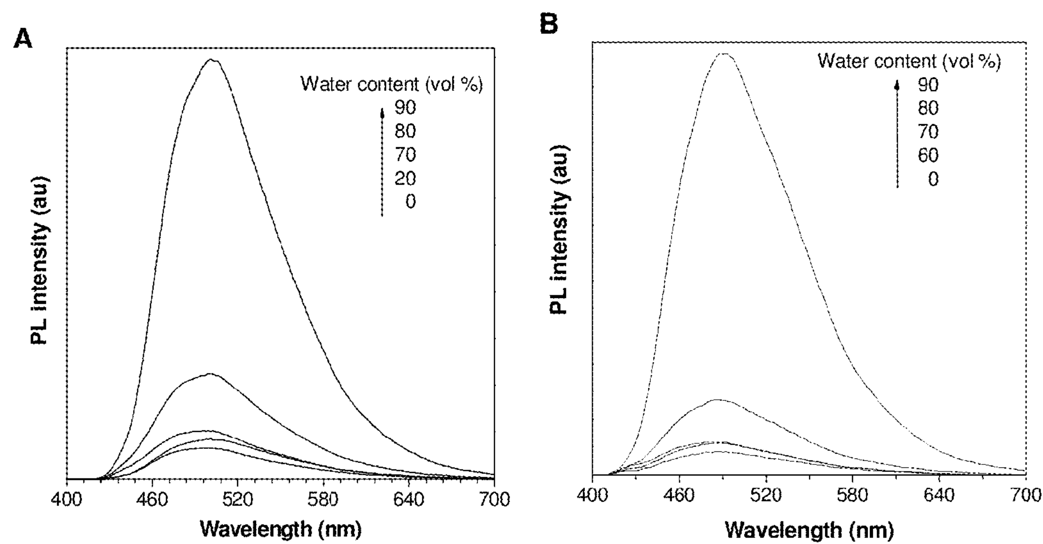
FIG. 3A illustrates the photoluminescence (PL) spectra of Silole-$C_1$ in THF/water mixtures with different water fractions ($f_w$).
FIG. 3B illustrates the PL spectra of Silole-$C_{10}$ in THF/water mixtures with different water fractions ($f_w$).
Figure 4:
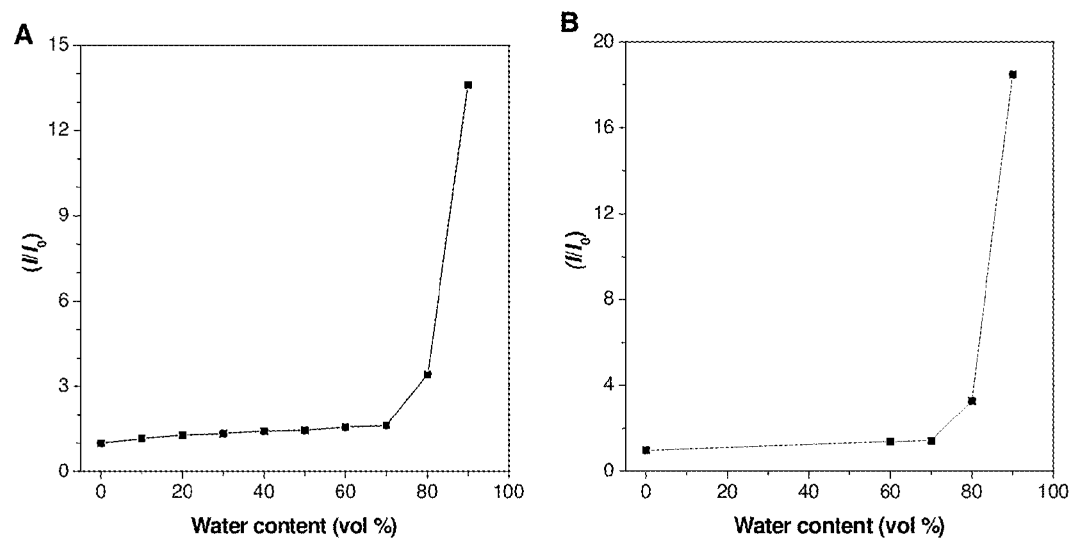
FIG. 4A illustrates the peak intensity of Silole-$C_1$ in relation to the water content (vol %) in the aqueous mixtures. [Silole-$C_1$]=10 μM; $\lambda_{ex}$=500 nm.
FIG. 4B illustrates the peak intensity of Silole-$C_{10}$ in relation to the water content (vol %) in the aqueous mixtures. [Silole-$C_{10}$]=10 μM; $\lambda_{ex}$=500 nm.

Single crystals of Silole-$C_1$ were grown from its methanol/THF mixture as large yellow blocks. A suitable specimen for crystallography was mounted in air on a glass fiber and its XRD intensity data was collected on a diffractometer. The Oak Ridge Thermal Ellipsoid Plot (ORTEP) of Silole-$C_1$ is shown in FIG. 1 and its crystal data are summarized in Table 1, below. While both Silole-$C_1$ and Silole-$C_{10}$ were weakly fluorescent when dissolved in THF, the addition of a large volume of water into THF greatly increased its fluorescence. (FIGS. 3 and 4). In the THF/water mixture with a water content ($f_w$) of 90 vol %, the fluorescence intensities (I) of Silole-$C_1$ and Silole-$C_{10}$ were about 19 times stronger than that of Silole-$C_1$ and Silole-$C_{10}$ in pure THF ($I_0$).

Figure 5:
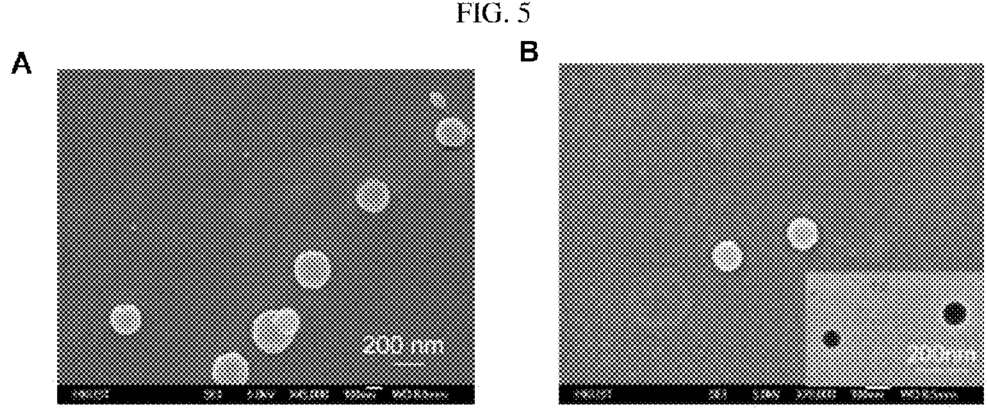
FIG. 5A shows a Scanning Electron Microscopy (SEM) image of nanoparticles of Silole-$C_1$ suspended in THF/water mixture (3:7 v/v).
FIG. 5B shows SEM and Transmission Electron Microscopy (TEM) images of nanoparticles of Silole-$C_1$ suspended in DMSO/water mixture (1:1000 v/v).
Figure 6:
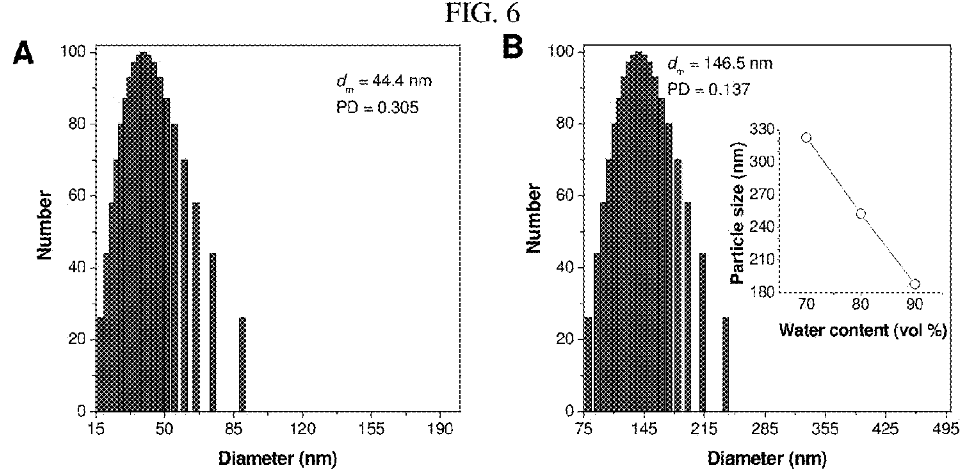
FIG. 6A illustrates the particle size distribution of Silole-$C_1$ in DMSO/PBS=1/1000 mixture ($d_m$=mean diameter, PD=polydispersity).
FIG. 6B illustrates the particle size distribution of Silole-$C_{10}$ in DMSO/PBS=1/1000 mixture and the variation of aggregate size of Silole-$C_{10}$ with water content of THF/water mixture.

As shown in FIGS. 5 and 6, Silole-$C_1$ nanoaggregates with an average diameter (d) of about 50 nm were formed in a DMSO/water mixture with an $f_w$ of 99.9%. Likewise, molecules of Silole-$C_{10}$ formed nanoaggregates in the aqueous mixtures (d~150 nm). The particle size decreased with an increase in the water content (FIG. 6), as observed in many other AIE luminogen systems. This indicates that the smaller particles are populated in the aqueous mixture with higher water content. Absolute fluorescence quantum yields of Silole-$C_1$ and Silole-$C_{10}$ were measured using an integrating sphere in the solid state and found to be 44.6% and 36.5%, respectively. All experimental data prove that the silole derivatives are AIE active.

Characterization Data for Silole-$C_1$: $^1$H NMR (400 MHz, $CDCl_3$), δ (ppm): 7.11-7.02 (m, 10H), 6.90-6.84 (m, 8H), 3.49 (m, 4H), 2.59-2.51 (m, 8H), 1.11-1.03 (m, 12H), 0.52-0.50 (s, 6H). $^{13}$C NMR (100 MHz, $CDCl_3$), δ (ppm): 153.7, 141.2, 139.1, 138.1, 136.9, 129.9, 128.6, 128.5, 127.3, 126.0, 57.1, 46.6, 29.5, 11.7, 11.6, −3.6. HRMS (MALDI-TOF): 584.2692 ([M]$^+$, calcd 584.3587).

TABLE 1

Crystal Data for Silole-$C_1$.

| | |
|---|---|
| Empirical formula | $C_{40}H_{48}N_2Si$ |
| Mol wt | 584.89 |
| Crystal dimensions, mm | 0.40 × 0.22 × 0.08 |
| Crystal system | Monoclinic |
| Space group | C2/C |
| a, Å | 25.8717(3) |
| b, Å | 10.04270(10) |
| c, Å | 14.41370(10) |
| α, deg | 90 |

TABLE 1-continued

| Crystal Data for Silole-$C_1$. | |
|---|---|
| β, deg | 96.8400(10) |
| γ, deg | 90 |
| V, $Å^3$ | 3460.36(6) |
| Z | 4 |
| $D_{calcd.}$, g $cm^3$ | 1.23 |
| $F_{000}$ | 1264 |
| Temp, (K) | 173(2) |
| μ (Mo Kα) $mm^{-1}$ | 0.803 |
| $2\theta_{max}$, deg (completeness) | 66.5 (88.4%) |
| No. of collected reflns. | 10967 |
| No. of unique reflns.($R_{int}$) | 2721 (0.0755) |
| Data/restraints/parameters | 2721/0/268 |
| $R_1$, $wR_2$ [obs I > 2σ (I)] | 0.0811, 0.1638 |
| $R_1$, $wR_2$ (all data) | 0.0841, 0.1651 |
| Residual peak/hole e.$Å^{-3}$ | 0.229/−0.274 |
| Transmission ratio | 1.00/0.66 |
| Goodness-of-fit on $F^2$ | 1.067 |

Characterization Data for Siliole-$C_{10}$: $^1$H NMR (400 MHz, $CDCl_3$), δ (ppm): 7.11 (m, 4H), 7.00 (m, 6H), 6.91 (m, 4H), 6.84 (m, 4H), 3.50 (m, 4H), 2.54-2.52 (m, 8H), 1.42-1.23 (m, 20H), 1.07-1.04 (m, 13H), 0.50 (s, 3H). $^{13}$C NMR (100 MHz, $CDCl_3$), δ (ppm): 154.3, 140.6, 139.1, 138.4, 136.7, 129.9, 128.6, 128.5, 127.2, 125.9, 57.1, 46.6, 32.8, 31.8, 29.5, 29.4, 29.3, 29.1, 23.5, 22.6, 14.0, 13.4, 11.6, −5.2. HRMS (MALDI-TOF): 710.5771 ($[M]^+$, calcd 710.4995).

Example 2

Cell Culture

HeLa and HEK 293T cells were cultured in the minimum essential medium (MEM) containing 10% fetal bovine serum and antibiotics (100 units/mL penicillin and 100 μg/mL streptomycin) in a 5% $CO_2$ humidity incubator at 37° C.

Example 3

Cell Viability Evaluated by MTT Assay

Viability of the cells was assayed using cell proliferation Kit I with the absorbance of 595 nm being detected using a Perkin-Elmer Victor plate reader. Five thousand cells were seeded per well in a 96-well plate. After overnight culture, various concentrations of siloles were added into the 96-well plate. After 24 h treatment, 10 μL of 3-(4,5-dimethyl-2-thiazolyl)-2,5-diphenyltetrazolium bromide (MTT) solution (5 mg/mL in phosphate buffer solution) was added into each well. After 2 h incubation at 37° C., 100 μL of solubilization solution containing 10% SDS and 0.01 M HCl was added to dissolve the purple crystals. After 24 h incubation, the optical density readings at 595 nm were taken using a plate reader. Each of the experiments was performed at least 3 times.

Figure 7:
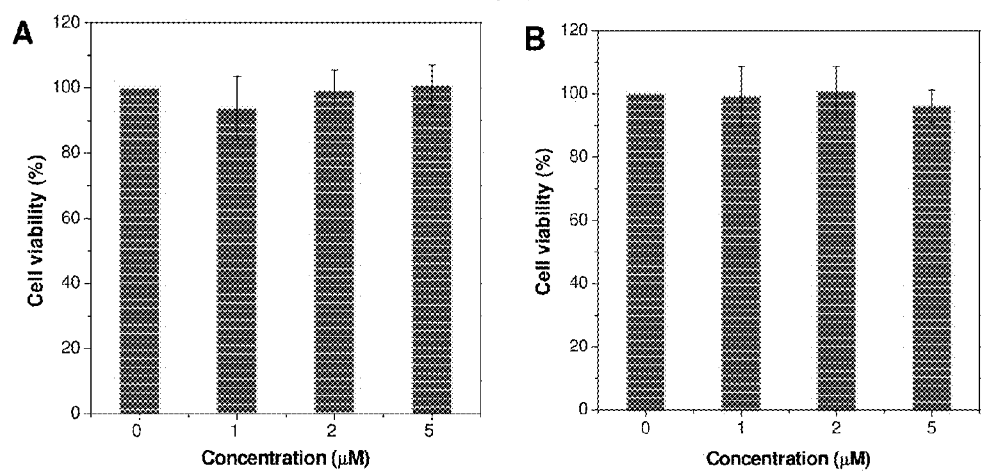
FIG. 7A illustrates the cytotoxicity of Silole-$C_1$ on HeLa cells determined by MTT assay.
FIG. 7B illustrates the cytotoxicity of Silole-$C_{10}$ on HeLa cells determined by MTT assay.

In the culture medium containing Silole-$C_1$, HeLa cells grew as normally as in the control run (FIG. 7A). Similar results were obtained for Silole-$C_{10}$ (FIG. 7B). Evidently, neither Silole-$C_1$ nor Silole-$C_{10}$ interfered with the cell physiology and proliferation within the tested concentration range (1-5 μM). This also demonstrated that the tiny amount (0.1%) of DMSO used in the MTT assay exerted little effect on the cell metabolism.

Example 4

Cell Imaging

The AIE luminogens were used to stain living cells. HeLa cells were grown overnight on a plasma-treated 25 mm round cover slip mounted to the bottom of a 35 mm petri dish with an observation window. The live cells were stained with either 5 μM of siloles for 45 min (by adding 1 μL of a 5 mM stock solution of siloles in DMSO to 1 mL culture medium) or 100 nM MTR for 15 min. The cells were imaged under an inverted FL microscope (Nikon Eclipse TE2000-U) using different combinations of excitation and emission filters for each dye: for siloles, excitation filter=330-380 nm, dichroic mirror=400 nm, and emission filter=420 nm long pass; for MTR, excitation filter=510-560 nm, dichroic mirror=575 nm, and emission filter=590 nm long pass; and for MTG, excitation filter=450-490 nm, dichroic mirror=505 nm, and emission filter=520 nm long pass. The obtained digital FL images were then processed using Spot software (Diagnostic Instruments, Inc.). The FL intensities were measured using Alpha EaseFC™ software (Alpha Innotech Corporation).

Figure 8:
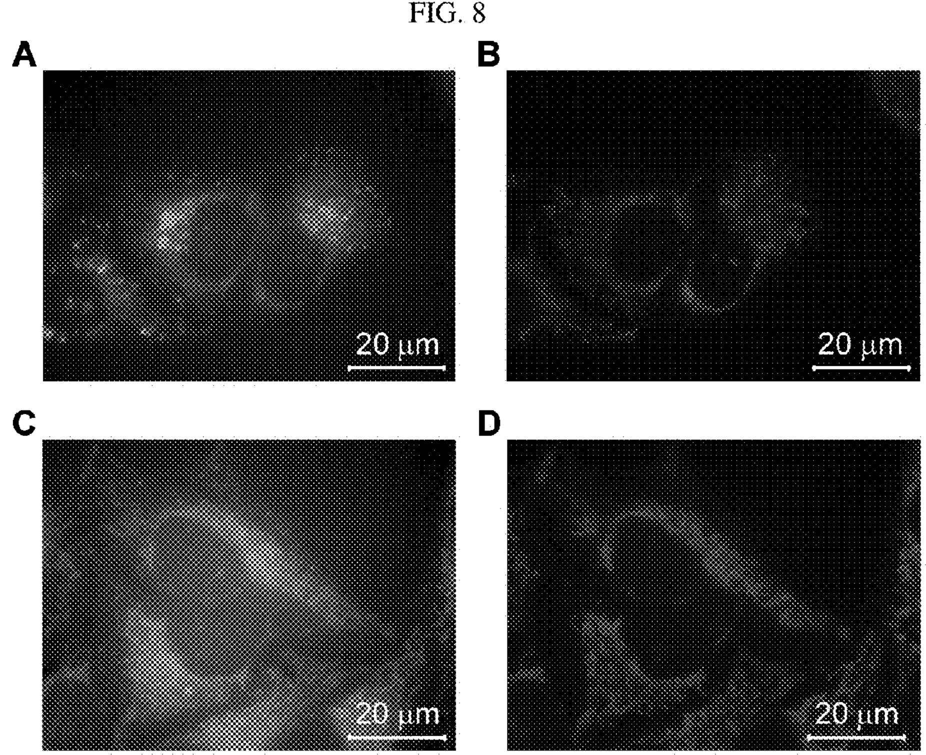
FIG. 8 illustrates fluorescent images of co-stained HeLa cells by (A) Silole-$C_1$, (B) Mitotracker Red CMXRos, (C) Silole-$C_{10}$ and (D) Mitotracker Red CMXRos. (Concentration of 1:5 μM).

Both Silole-$C_1$ and Silole-$C_{10}$ stained cytoplasmic regions of HeLa cells but not their nucleic parts (FIGS. 8A and C). As some of the imaged filamentous structures looked like mitochondria, control experiments were run using a commercially available mitochondrion-selective dye, MitoTracker Red CMXRos (MTR). The staining pattern of MTR (FIGS. 8B and D) was similar to that of Silole-$C_1$ and Silole-$C_{10}$, which indicates that the silole nanoaggregates are mainly localized in the mitochondrial regions. The cytoplasmic areas stained by the aggregates, however, were larger than the mitochondrial regions. Since Silole-$C_1$ and Silole-$C_{10}$ are hydrophobic, it is likely that the molecules entered other membrane-bound organelles, such as endoplastic reticula.

Figure 9:
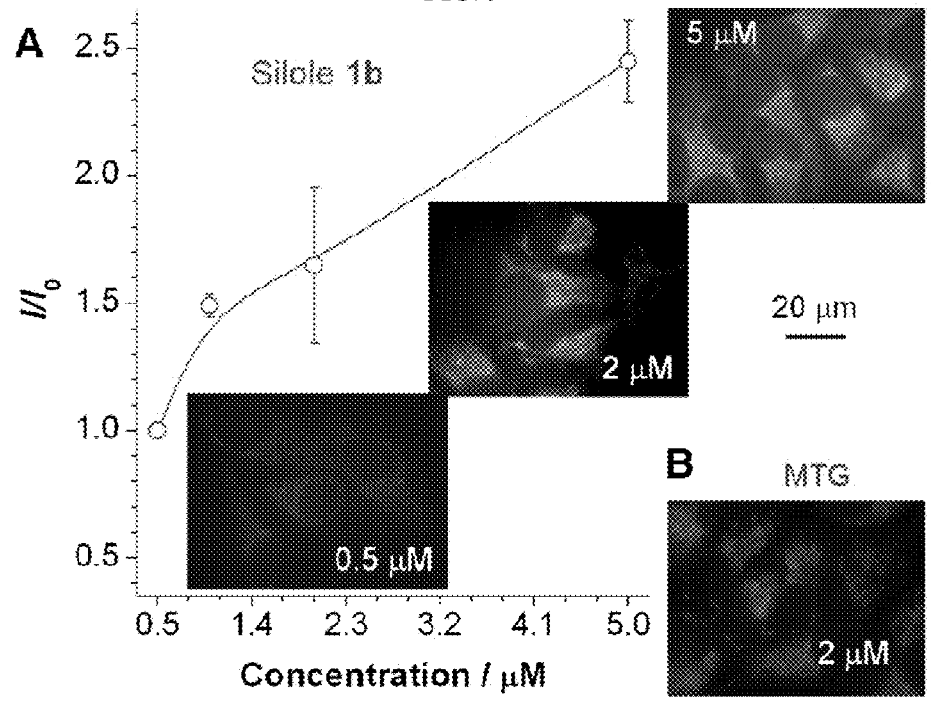
FIG. 9A illustrates $I/I_0$ in relation to the concentration of Silole-$C_{10}$ in the culture medium of HeLa cells. ($I_0$=intensity of the cells stained by 0.5 μM of Silole-$C_{10}$.) Inset: fluorescent images of the living cells stained by different amounts of Silole-$C_{10}$ for 45 min.
FIG. 9B illustrates the fluorescent image of HeLa cells stained by 2 μM of MitoTracker Green FM (MTG) for 45 min.
Figure 10:
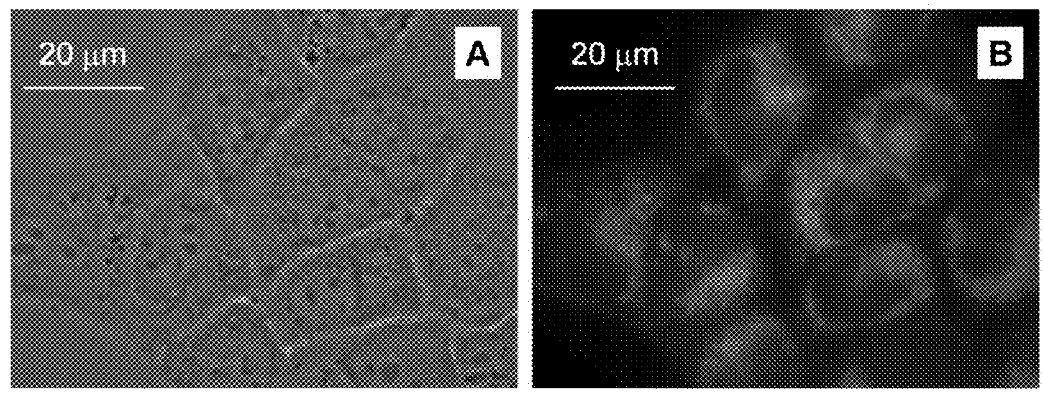
FIG. 10A shows the phase contrast image of HeLa cells stained with 5 μM MTG for 45 min.
FIG. 10B shows the fluorescent image of HeLa cells stained with 5 μM MTG for 45 min.

The fluorescence intensity of the HeLa cells stained by Silole-$C_{10}$ increased with increasing silole concentration (FIG. 9A), which is completely opposite from traditional dye systems which suffer from the ACQ effect discussed above. Organic dyes have often been functionalized with ionic groups to improve their water miscibility and are used in small quantities to obstruct their aggregate formation (e.g., working concentration suggested for MitoTracker Green FM (MTG) is in the range of ~20-200 nM). Addition of such ionic dyes into growth media may raise ionic strength, affect membrane potential and cause cell impairment. Indeed, when 2 μM MTG was used to stain the HeLa cells, their mitochondrial structures were partly damaged (FIG. 9B), probably because the electrostatic interactions had become too hostile and the oxidation and conjugation reactions had proceeded to intolerable extents at the "high" dye concentration. Even more severe damage was done to the cells when they had been incubated in the presence of 5 μM MTG (FIG. 10). In sharp contrast, the cells were maintained as healthy in the presence of 5 μM Silole-$C_{10}$ (FIGS. 8C and 9A), indicative of a high cytophilic level of the AIE luminogen. Silole-$C_{10}$ is a neutral luminogen carrying no ionic units. Its nanoaggregates in the growth medium are internalized by the cells and settle in the organelles via physical processes and not chemical reactions. The benignant interactions of Silole-$C_{10}$ with the cells have endowed it with superb cytocompatibility and enabled its use as a bioprobe at high concentrations.

Figure 11:
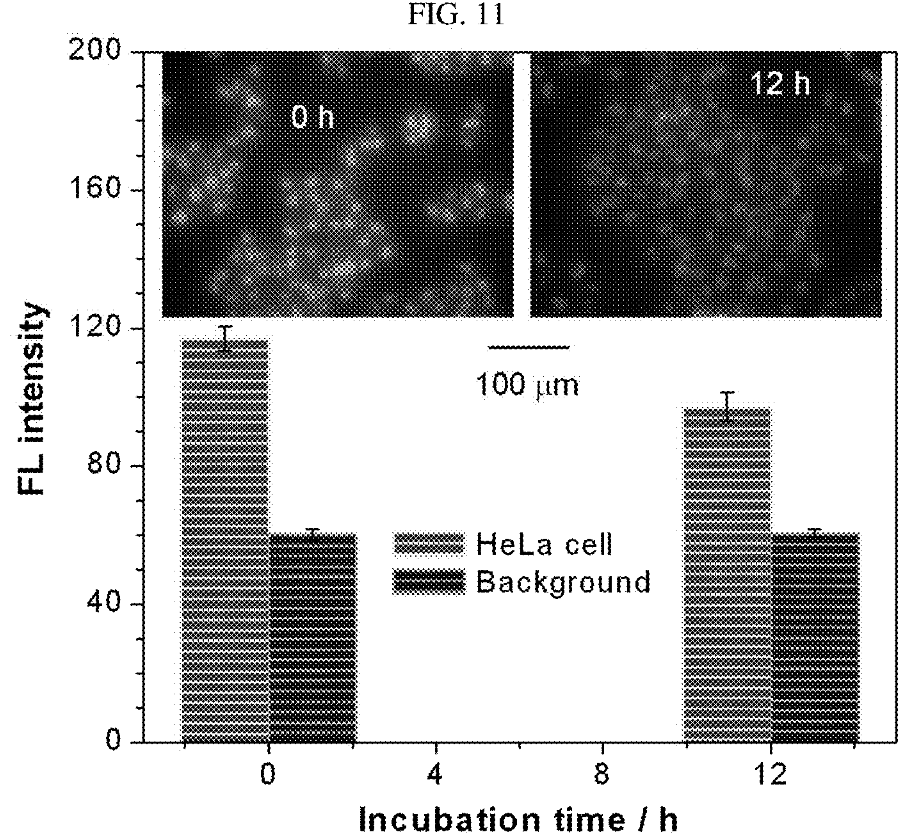
FIG. 11 illustrates the fluorescent intensities of Silole-$C_{10}$ (5 μM) and the auto-fluorescence (background) of HeLa cells before and after incubation in fresh culture media for 12 hours.

The cellular internalization and fluorescence "turn-on" of Silole-$C_{10}$ occurred via physical processes. The nanoaggregates were fully retained in the living cells, even after the stained HeLa cells had been incubated in a fresh medium for 12 h (FIG. 11). The cytophilic nature of Silole-$C_{10}$ and its hydrophobic interactions with the membrane-enclosed organelles may account for the leak-free lodging of its nanoaggregates inside the cells. Few conventional dyes can be retained in viable cells for more than a couple of hours under physiological conditions because of reverse diffusion of the free dye molecules. Although some Cell-Tracker probes can stay in living cells through a few generations, both of their intracellular fixation and FL activation are realized by chemical reactions (e.g., conjugation, oxidation and hydrolysis), which can be cytotoxic.

Example 5

Co-culture of HeLa and HEK-293T Cells

HeLa cells stained by Silole-$C_{10}$ were co-cultured with pure HEK 293T cells, in an effort to determine whether Silole-$C_{10}$ can be used to discriminate between different cell lines. The HeLa and HEK cells were used in the co-culture test because of their readily discernible morphologies.

HeLa cells were stained with 5 μM of Silole-$C_{10}$ or 200 nM of MTG (the high end of its suggested working concentrations) for 24 h. The stained HeLa and unstained HEK cells were detached from their respective culture dishes by treating with trypsin-EDTA solution and then one quarter of each type of the cells were re-suspended with 5 mL of MEM and transferred into a new 100 mm Petri dish. After 24 h incubation at 37° C., both phase contrast and fluorescence images of the co-cultured cells were obtained from the same region. The HeLa cells stained by Silole-$C_{10}$ were still very emissive after co-culture with the HEK cells for 24 h, whereas almost no fluorescence signal was detectable in the MTG-stained HeLa cells.

Figure 13:
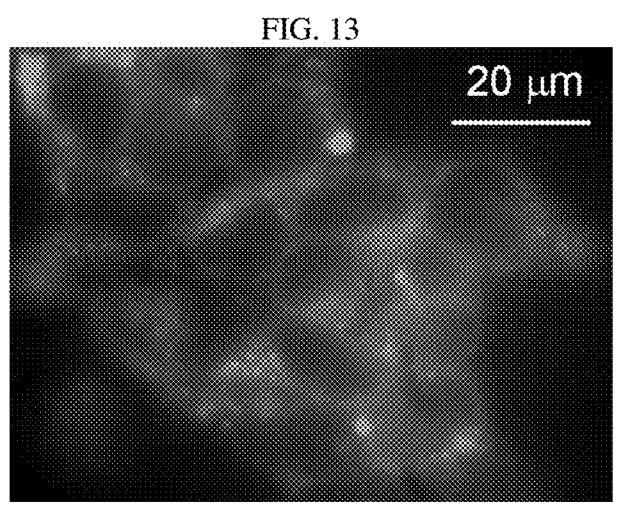
FIG. 13 shows the fluorescence image of HEK-293T cells stained by Silole-$C_{10}$ in DMSO/water mixture (1:1000 v/v) for 45 min.
Figure 14:
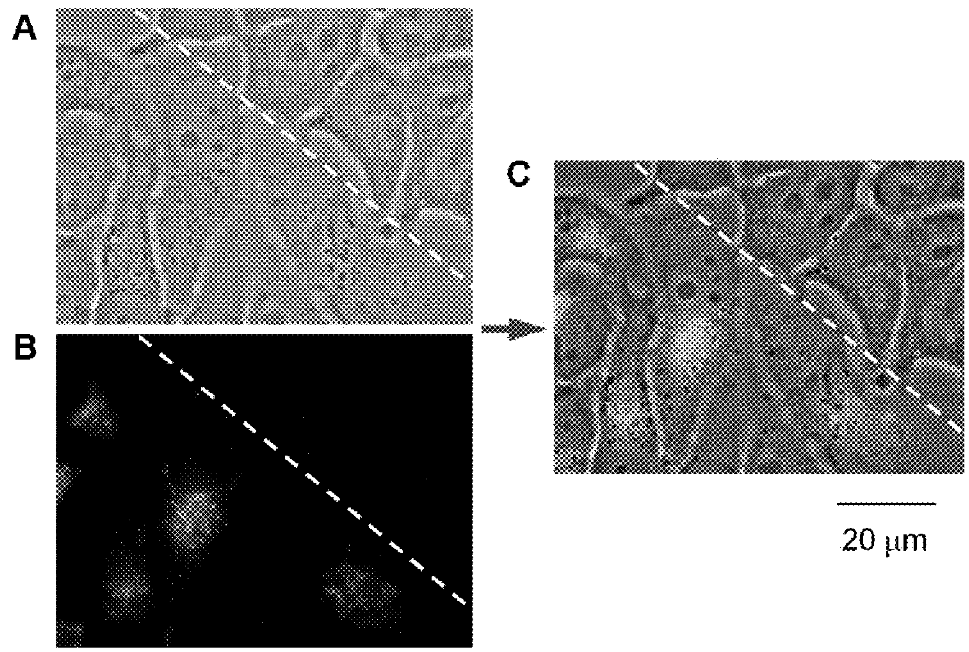
FIG. 14A shows the phase contrast image of the Silole-$C_{10}$ stained HeLa cells co-cultured with unstained HEK 293T cells.
FIG. 14B shows the fluorescence image of the Silole-$C_{10}$ stained HeLa cells co-cultured with unstained HEK 293T cells.
FIG. 14C shows the overlapping image of the Silole-$C_{10}$ stained HeLa cells co-cultured with unstained HEK 293T cells.
Figure 15:
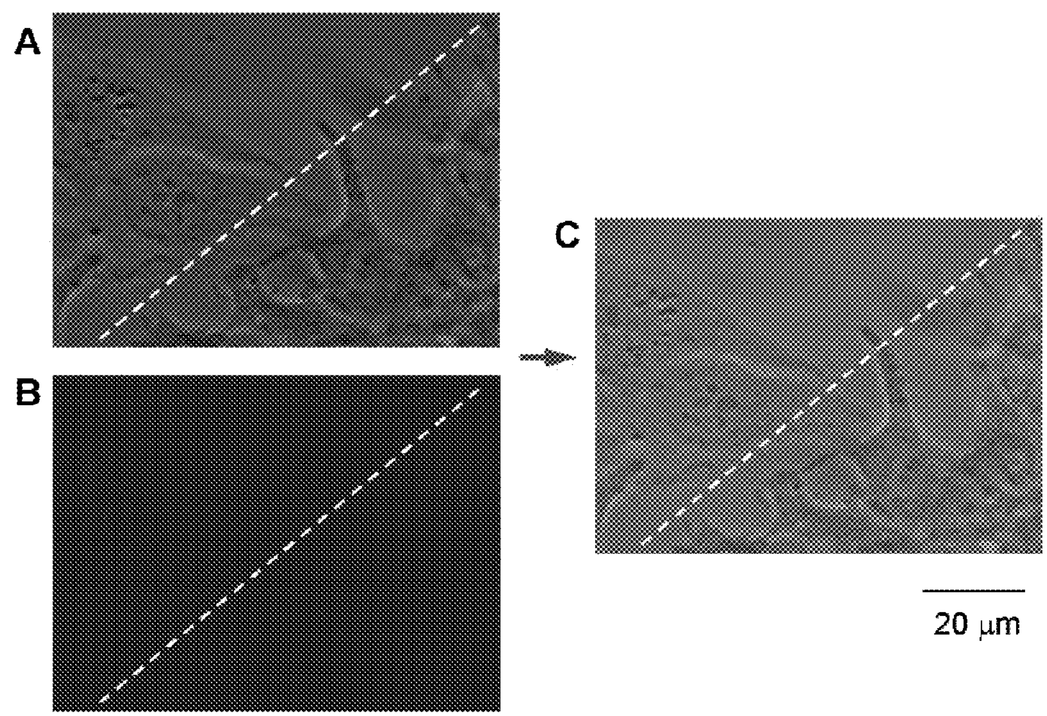
FIG. 15A shows the phase contrast image of the MTG-stained HeLa cells co-cultured with unstained HEK 293T cells.
FIG. 15B shows the fluorescence image of the MTG-stained HeLa cells co-cultured with unstained HEK 293T cells.
FIG. 15C shows the overlapping image of the MTG-stained HeLa cells co-cultured with unstained HEK 293T cells.

Although the nanoaggregates of Silole-$C_{10}$ could readily stain the HEK cells in the homo-culture test (FIG. 13), the nanoaggregates stayed in the HeLa cells without penetrating into the HEK cells after the two types of cells had been co-cultured in a Petri dish for a whole day, indicating that the nanoaggregates were firmly retained inside the HeLa cells (FIG. 14). In contrast, MTG failed to function because of its low working concentration and fast leakage (FIG. 15). Therefore, the HeLa cells stained by MTG could not be distinguished from the unstained HEK cells in the co-culture test.

The excellent intracellular retention of the aggregates of Silole-$C_{10}$ make it useful as a fluorescent biosensor for distinguishing between cancerous and normal cells and for tracing invasion, diffusion and spread as well as suppression, shrinkage and necrosis processes of tumor cells.

Example 6

Long Time Cell Tracking

The possibility that Silole-$C_{10}$ may be used for long-term cell tracing was tested by staining HeLa cells grown on a Petri dish at 50% confluence with 5 μM of Silole-$C_{10}$. The cells were imaged under an inverted fluorescence microscope. After taking an image at the end of 24 h of incubation, referred to as the end of the 1st passage, 25% of the cells in the completely filled Petri dish were transferred to a new dish with a fresh growth medium. Another image was taken after 24 h in the then half-filled Petri dish, i.e., the end of the 2nd passage. The cells were further incubated for another 24 h, i.e., to the end of the 3rd passage. The process was repeated to proceed to the 4th passage. The luminogen was able to trace the living cells for four passages, a period close to 100 h, proving that Silole-$C_{10}$ is a superb long-term cell tracer.

Figure 12:
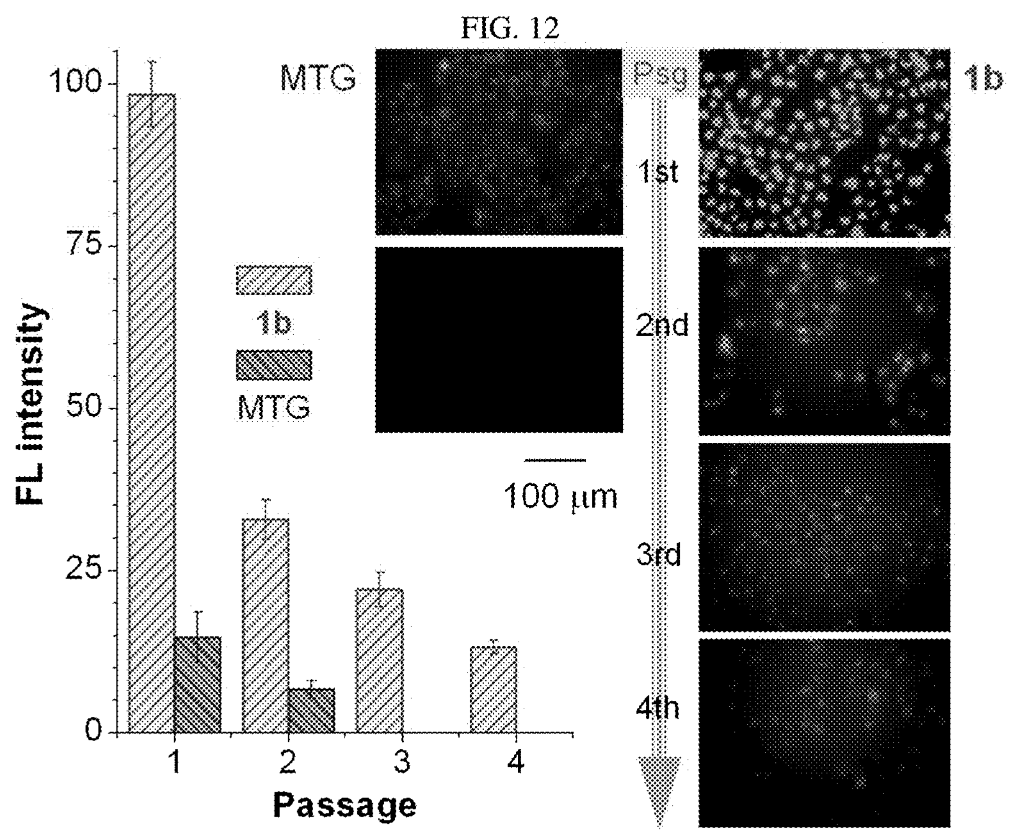
FIG. 12 illustrates the fluorescence intensities and images of living HeLa cells stained by 5 μM of Silole-$C_{10}$ and 200 nM of MTG at different passages.

The images for Silole-$C_{10}$ were compared with those for MTG, obtained following the protocol described above for Silole-$C_{10}$ at an [MTG] of 200 nM (the high end of its suggested working concentrations). The HeLa cells stained by Silole-$C_{10}$ after the first passage were clearly more emissive than the corresponding cells stained by MTG (FIG. 12). The cells stained by Silole-$C_{10}$ were still visible even after four passages, whereas almost no fluorescence signal was detectable in the MTG-stained cells after only two passages. Therefore, the luminogen was able to trace the living cells for a period close to 100 h, proving that Silole-$C_{10}$ is indeed a superb long-term cell tracer.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. A method of preparing a fluorescent bioprobe comprising luminogen formed nanoparticles for cellular imaging and long term cellular tracking comprising one or more luminogens that exhibit aggregation-induced emission properties, wherein the luminogen formed nanoparticles are fully retained inside living cells and have a fluorescence emission;

wherein the one or more luminogens have the structure:

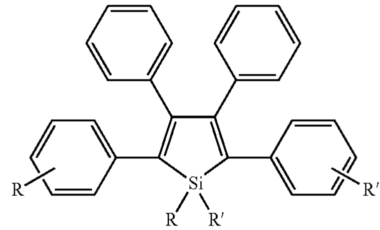

wherein

R and R' are independently selected from the group consisting of H, $C_nH_{2n+1}$, $OC_nH_{2n+1}$, $C_6H_5$, $OC_6H_5$, and $(X)_nN[(CH_2)_mCH_3]_2$;

X is selected from the group consisting of $(CH_2)_n$, $C_6H_5$, and $O(CH_2)_n$; and n, m independently=an integer from 0 to 20, wherein when both the R and R' groups attached to the Si atom are $C_6H_5$, at least one of the R and R' groups attached to the phenyl rings is other than H;

comprising:

(a) preparing an organic solution of the one or more luminogens;

(b) mixing the organic solution into an aqueous medium; and (c) removing the organic solvent to form the luminogen formed nanoparticles.

2. The method of claim 1, wherein the one or more luminogens have the structure:

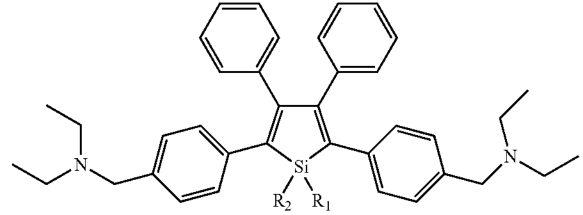

wherein $R_1$ is $CH_3$ and $R_2$ is selected from the group consisting of $CH_3$ and $C_{10}H_{21}$.

3. The method of claim 1, wherein the one or more luminogens have noncovalent interactions, including hydrophobic interactions, with biomolecules inside cells.

4. The method of claim 1, wherein the luminogen formed nanoparticles are 1 nm to 100,000 nm in size.

5. The method of claim 1, further comprising step d) staining living cells in a cell culture medium with the luminogen formed nanoparticles.

6. A method of in vitro cellular imaging comprising contacting target cells with a fluorescent bioprobe comprising luminogen formed nanoparticles for cellular imaging and long term cell tracking comprising one or more luminogens that exhibit aggregation-induced emission properties;

wherein the luminogen formed nanoparticles are fully retained inside living cells and have a fluorescence emission;

wherein the one or more luminogens have the structure:

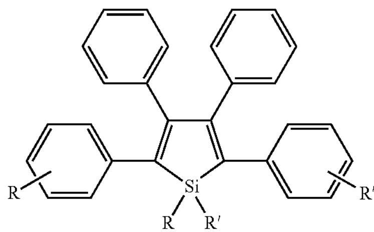

wherein

R and R' are independently selected from the group consisting of H, $C_nH_{2n+1}$, $OC_nH_{2n+1}$, $C_6H_5$, $OC_6H_5$, and $(X)_nN[CH_2)_mCH_3]_2$;

X is selected from the group consisting of $(CH_2)_n$, $C_6H_5$, and $O(CH_2)_n$; and n, m independently=an integer from 0 to 20, wherein when both the R and R' groups attached to the Si atom are $C_6H_5$, at least one of the R and R' groups attached to the phenyl rings is other than H; and detecting cellular fluorescence.

7. The method of claim 6, wherein the target cells are live cells.

8. The method of claim 7, wherein the fluorescent bioprobes can stay inside the target cells for at least 95 hours without leaking out.

9. The method of claim 6, wherein the fluorescent bioprobes can stay inside the target cells for at least four passages without leaking out.

10. The method of claim 6, wherein the target cells are cancer cells or cells that can preferentially accumulate in tumors.

11. The method of claim 10 further comprising determining whether a tumor or cancer cells are present.

12. The method of claim 6, wherein the target cells are selected from the group consisting of HeLa cells and HEKT-293 cells.

13. The method of claim 6, wherein the in vitro cellular imaging further comprises live cell tracking.

14. The method of claim 6, wherein the in vitro cellular imaging further comprises long term cellular tracking.

* * * * *